United States Patent
Booth

(10) Patent No.: US 10,548,856 B2
(45) Date of Patent: Feb. 4, 2020

(54) COMPOUNDS AND METHODS FOR MODULATING SEROTONIN RECEPTORS IN THE PERIPHERY

(71) Applicant: Northeastern University, Boston, MA (US)

(72) Inventor: Raymond G. Booth, Arlington, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/574,971

(22) PCT Filed: May 19, 2016

(86) PCT No.: PCT/US2016/033185
§ 371 (c)(1),
(2) Date: Nov. 17, 2017

(87) PCT Pub. No.: WO2016/187377
PCT Pub. Date: Nov. 24, 2016

(65) Prior Publication Data
US 2018/0125798 A1  May 10, 2018

Related U.S. Application Data

(60) Provisional application No. 62/163,652, filed on May 19, 2015.

(51) Int. Cl.
| | | |
|---|---|---|
| *A61K 31/135* | (2006.01) | |
| *A61K 9/00* | (2006.01) | |
| *A61P 9/00* | (2006.01) | |
| *A61P 9/12* | (2006.01) | |
| *A61P 1/00* | (2006.01) | |
| *A61P 1/04* | (2006.01) | |

(52) U.S. Cl.
CPC .......... *A61K 31/135* (2013.01); *A61K 9/0053* (2013.01); *A61P 1/00* (2018.01); *A61P 1/04* (2018.01); *A61P 9/00* (2018.01); *A61P 9/12* (2018.01)

(58) Field of Classification Search
CPC ... G09G 2310/0267; G09G 2310/0286; G09G 3/20; G09G 3/36; G11C 19/28; H01L 27/1214
See application file for complete search history.

(56) References Cited

U.S. PATENT DOCUMENTS

2006/0293309 A1  12/2006  Thor et al.

FOREIGN PATENT DOCUMENTS

| WO | 2008/156707 A1 | 12/2008 |
| WO | 2009/061436 A1 | 5/2009 |
| WO | 2010/129048 A1 | 11/2010 |

OTHER PUBLICATIONS

West, Anthony R., Solid State Chemistry and its Applications, Wiley, New York, 1988, 358. (Year: 1988).*
Wyrick, et al., 1-Phenyl-3-amino-1,2,3,4-tetrahydronaphthalenes and Related Derivatives as Ligands for the Neuromodulatory σ3 Receptor: Further Structure—Activity Relationships, J. Med. Chem., 38, 3857-3864 (1995). (Year: 1995).*
PUBCHEM-CID 42601571 (Create Date: Jun. 8, 2009) 10 pgs.
C.E. Canal et al., "An Orally Active Phenylaminotetralin-Chemotype Serotonin 5HT7 and 5-HT1A Receptor Partial Agonist That Corrects Motor Stereotypy in Mouse Models", ACS Chemical Neuroscience, (2015), vol. 6, pp. 1259-1270.
E.C. Bucholtz, et al., "Synthesis, Evaluation, and Comparative Molecular Field Analysis of 1-Phenyl-3-amino-1,2,3,4-tetrahydronaphthalenes as Ligands for Histamine H1 Receptors", J. Med. Chem., (1999), vol. 42, pp. 3041-3054.
S.D. Wyrick, et al., "1-Phenyl-3-amino-1,2,3,4-tetrahydronaphthalenes and Related Derivatives as Ligands for the Neuromodulaory σ3 Receptor: Further Structure-Activity Relationships", J. Med. Chem. (1995), vol. 38, pp. 3857-3864.

* cited by examiner

*Primary Examiner* — Erich A Leeser
(74) *Attorney, Agent, or Firm* — Verrill Dana, LLP

(57) ABSTRACT

This invention relates to, in part, compositions and methods that are useful for, inter alia, the treatment of various diseases, including those linked to binding at a serotonin receptor in the GI tract.

28 Claims, No Drawings

COMPOUNDS AND METHODS FOR MODULATING SEROTONIN RECEPTORS IN THE PERIPHERY

This application claims the benefit of U.S. Provisional Application No. 62/163,652, filed on 19 May 2015 and entitled "Compounds and Methods for Modulating Serotonin Receptors in the Periphery", which is incorporated herein by reference in its entirety.

FIELD OF THE INVENTION

This invention relates to, in part, compositions and methods that are useful for the treatment of various diseases, including those linked to serotonin receptor binding, such as, for example, gastrointestinal and cardiopulmonary disorders or conditions.

BACKGROUND

The gastrointestinal (GI) tract is the largest producer of serotonin (5-hydroxytryptamine (5-HT)) in the body, and as such it is intimately connected with GI function and physiology. Serotonin produced by enterochromaffin (EC) cells is an important enteric mucosal signaling molecule and has been implicated in a number of gastrointestinal disorders or conditions, including inflammatory bowel disease and irritable bowel syndrome.

Alosetron (LOTRONEX), a 5-HT$_3$ receptor antagonist, became the first agent approved by the US Food and Drug Administration for the treatment of diarrhea-predominant IBS in 2000. However, the drug has demonstrated a difficult post-approval side effect profile that has resulted in a temporary market withdrawal. Meanwhile, activation of the serotonin 5-HT$_{2B}$ receptor is linked to cardiac valvulopathy and pulmonary hypertension (Fitzgerald et al. Mol Pharmacol. 2000; 57: 75-81; Setola et al. Mol Pharmacol. 2005 68:20-33, Launay J et al. Nat Med 2002 8: 1129-1135), and attenuation of 5-HT$_{2B}$ receptor signaling may prevent and/or reverse cardiopulmonary disorders (Janssen et al. Biomed Res Int. 2015; 2015:438403; Rothman et al. Expert Opin Drug Saf. 2009 May; 8(3):317-29).

There remains a need for agents that can safely modulate serotonin receptors (5-hydroxytryptamine receptors or 5-HT receptors) for the treatment of gastrointestinal and cardiopulmonary disorders or conditions.

SUMMARY OF THE INVENTION

Accordingly, the present invention provides for compositions and methods that agonize or antagonize one or more serotonin receptors and which find use in, for example, the treatment of various gastrointestinal or cardiopulmonary disorders or conditions.

In one aspect, the invention provides a compound, or a pharmaceutical composition comprising a compound, having the structure of Formula I or Formula II:

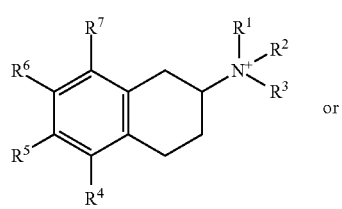

or

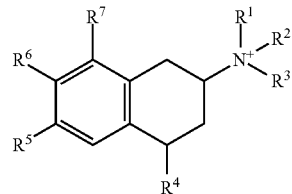

where R$^1$ to R$^7$ are hydrogen or independently selected substituents. Suitable substituents are disclosed herein. In various embodiments, none of R$^1$, R$^2$, and R$^3$ is hydrogen. For example, in some embodiments, R$^1$, R$^2$, and R$^3$ are alkyl, e.g. methyl, or may come together to form a heterocyclic ring and each of R$^4$, R$^5$, R$^6$, and R$^7$ is independently hydrogen, hydroxy, sulfoxy, halo, acyl, acyloxy, alkyl, heteroalkyl, alkenyl, heteroalkenyl, alkynyl, heteroalkynyl, alkoxy, cycloalkyl, heterocycloalkyl, aryl, arylalkyl, arylhalo, arylhydroxy, arylcyano, aryltrifluoromethyl, aryltrifluoromethoxy, arylnitro, aryltrifluoromethoxy, arylnitro, and arylether, arylester, arylsulfonyl, arylsulfinyl, arylsulfonamidyl, arylsulfonate, arylsulfoxyl, arylphosphate ester, arylcarbonyl, arylcarboxylate, arylcarbamate, arylamine, arylimide, heteroaryl, heteroarylalkyl, heteroarylhalo, heteroarylhydroxy, heteroarylcyano, heteroaryltrifluoromethyl, aryltrifluoromethoxy, arylnitro, heteroaryltrifluoromethoxy, heteroarylnitro, and heteroarylether, heteroarylester, heteroarylsulfonyl, heteroarylsulfinyl, heteroarylsulfonamidyl, heteroarylsulfonate, heteroarylsulfoxyl, heteroarylphosphate ester, heteroarylcarbonyl, heteroarylcarboxylate, heteroarylcarbamate, heteroarylamine, heteroarylimide, quinidine, morpholine, and any ring structure is optionally substituted with any of the substituents described herein, with the proviso that any two adjacent substituents can come together to form a carbocyclic or heterocyclic ring system.

In various embodiments, any of R$^4$, R$^5$, R$^6$, and R$^7$ is a hydrocarbon or heterocyclic ring system. In some embodiments, the hydrocarbon or heterocyclic ring system is independently selected from phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyzazinyl, pyrimidinyl, oxadiazolyl, benzimidazolyl, and triazinyl, each of which may contain substituents (i.e. is optionally substituted). In some embodiments, the heterocyclic ring system may contain one or more heteroatoms selected from the group consisting of oxygen, sulfur, nitrogen, and combinations thereof.

In a specific embodiment, only R$^4$ is a hydrocarbon or heterocyclic ring system which is optionally substituted. In a specific embodiment, only R$^4$ is a hydrocarbon or heterocyclic ring system which is optionally substituted, all of R$^1$, R$^2$, and R$^3$ are alkyl, and each of R$^5$, R$^6$, and R$^7$ is independently hydrogen, hydroxy, sulfoxy, halo, acyloxy, alkyl, heteroalkyl, alkenyl, heteroalkenyl, alkynyl, heteroalkynyl, acyl, and alkoxy.

In various embodiments the compound or composition does not substantially accumulate in the human brain. In various embodiments the compound or composition is not rapidly metabolized in the periphery. In various embodiments the nitrogen bearing R$^1$, R$^2$, and R$^3$ in the above formulae is positively charged. For example, in various embodiments, the compound or composition of the invention has the structure of Formula I or Formula II and all of R$^1$, R$^2$, and R$^3$ are alkyl groups, including methyl, ethyl, propyl, isopropyl, n-butyl, iso-butyl, sec-butyl isobutyl, tertiary butyl, pentyl, isopentyl, neopentyl, and hexyl, which may be optionally substituted. In various embodiments, all of $R^1$, $R^2$, and $R^3$ are identical alkyl groups. In various embodiments, two of or three of $R^1$, $R^2$, and $R^3$ are different alkyl groups. In some embodiments, $R^1$, $R^2$, and $R^3$ are each methyl.

In various embodiments, the compound or composition is a modulator of one or more of $5\text{-HT}_1$ receptors (e.g. one or more of $5\text{-HT}_{1A}$, $5\text{-HT}_{1B}$, $5\text{-HT}_{1C}$, $5\text{-HT}_{1D}$, $5\text{-HT}_{1E}$, $5\text{-HT}_{1F}$); $5\text{-HT}_2$ receptors (e.g. one or more of $5\text{-HT}_{2A}$, $5\text{-HT}_{2B}$, $5\text{-HT}_{2C}$); $5\text{-HT}_3$ receptors; $5\text{-HT}_4$ receptors; $5\text{-HT}_5$ receptors (e.g. $5\text{-HT}_{5A}$); $5\text{-HT}_6$ receptors; and $\text{HT}_7$ receptors. In some embodiments, the modulated 5-HT receptor is present in the GI tract (e.g. one or more of the stomach, small intestine, large intestine and rectum and includes all subsections thereof (e.g. duodenum, jejunum and ileum, colon transversum, colon descendens, colon ascendens, colon sigmoidenum and cecum).

In various embodiments, the compound or composition is substantially enantiomerically pure. In some embodiments, the composition comprises at least about 70%, or at least about 80%, or at least about 85%, or at least about 90%, or at least about 95%, or at least about 97%, or at least about 99% of a single enantiomer. In various embodiments, a least about 85%, or at least about 90%, or at least about 95%, or at least about 97%, or at least about 99% of a single enantiomer. In some embodiments, the single enantiomer has functional properties (e.g. serotonin receptor selectivity and/or receptor affinity) that are not found in a corresponding enantiomer.

In various embodiments, the pharmaceutical compositions of the invention are formulated for long-action or sustained-release. In some embodiments, the formulation is suitable for oral delivery and/or transmucosal delivery (e.g. a capsule, tablet, patch, or lozenge).

In some aspects, the present invention relates to method for treating or preventing a gastrointestinal disorder or condition, optionally selected from inflammatory bowel disease, irritable bowel syndrome, celiac disease, and an enteric infection, comprising administering the compound or composition described herein to a patient in need thereof.

In some aspects, the present invention relates to a method for treating or preventing a functional GI disorder comprising administering the composition described herein to a patient in need thereof.

In some aspects, the present invention relates to a method for treating or preventing a cardiopulmonary disorder comprising administering the composition described herein to a patient in need thereof.

DETAILED DESCRIPTION OF THE INVENTION

The present invention is based, in part, on the discovery of novel serotonin receptor-modulating compounds that do not substantially accumulate in the brain and therefore are useful in treating diseases or disorders of the periphery, including gastrointestinal or cardiopulmonary disorders or conditions.

In some aspects, the invention provides a compound, or a pharmaceutical composition, comprising a compound, having the structure of Formula I or Formula II:

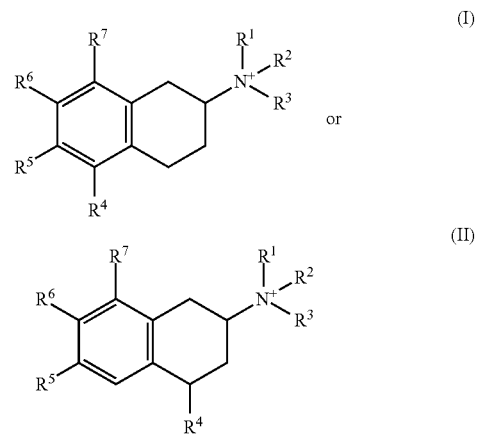

where each of $R^1$, $R^2$, $R^3$, $R^4$, $R^5$, $R^6$, and $R^7$ is hydrogen or a substituent, for example, as defined above.

In various embodiments, any of $R^4$, $R^5$, $R^6$, and $R^7$ is a hydrocarbon or heterocyclic ring system. In some embodiments, the hydrocarbon or heterocyclic ring system is independently selected from phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyzazinyl, pyrimidinyl, oxadiazolyl, benzimidazolyl, and triazinyl, each of which may contain substituents (i.e. is optionally substituted). In some embodiments, the heterocyclic ring system may contain one or more heteroatoms selected from the group consisting of oxygen, sulfur, nitrogen, and combinations thereof.

In a specific embodiment, only $R^4$ is a hydrocarbon or heterocyclic ring system which is optionally substituted. In a specific embodiment, only $R^4$ is a hydrocarbon or heterocyclic ring system which is optionally substituted, each of $R^1$, $R^2$, and $R^3$ is alkyl, and each of $R^5$, $R^6$, and $R^7$ is independently hydrogen, hydroxy, sulfoxy, halo, acyloxy, alkyl, heteroalkyl, alkenyl, heteroalkenyl, alkynyl, heteroalkynyl, acyl, and alkoxy. In these embodiments, the total number of atoms that comprise $R_4$ may be at least about 5, and not more than about 20 atoms, not including hydrogen atoms (e.g. between about 5 to about 10 non-hydrogen atoms, or between about 5 to about 15 non-hydrogen atoms, or between about 10 to about 15 non-hydrogen atoms).

In various embodiments the nitrogen bearing $R^1$, $R^2$, and $R^3$ in the above formulae is positively charged (e.g. a quaternary ammonium). For example, in various embodiments, the compound or composition of the invention has the structure of Formula I or Formula II and all of $R^1$, $R^2$, and $R^3$ are alkyl groups, including methyl, ethyl, propyl, isopropyl, n-butyl, iso-butyl, sec-butyl isobutyl, tertiary butyl, pentyl, isopentyl, neopentyl, and hexyl, which may be optionally substituted. In various embodiments, all of $R^1$, $R^2$, and $R^3$ are identical alkyl groups (e.g., methyl). In various embodiments, two of or three of $R^1$, $R^2$, and $R^3$ are different alkyl groups.

The compounds of Formula I may be referred to herein as "5-PAT" or "5-APT" compounds. The compounds of Formula II may be referred to herein as "4-PAT" or "4-APT" compounds. "PAT" is 1-Phenyl-3-dimethylaminotetralin. Such nomenclature is derived from the position of the attachment of $R_4$ to the bicyclic core of Formula I or Formula II, i.e. the tetrahydronaphthyl (tetralin) moiety bearing substituents $R^1$-$R^3$ and $R^5$-$R^7$.

In some embodiments, each of $R^1$, $R^2$, $R^3$, $R^4$, $R^5$, $R^6$, and $R^7$ is independently hydrogen, alkyl, aryl, halo, nitro, amino, heteroaryl, cycloalkyl, heterocyclic, or alkoxy. In various embodiments, none of $R^1$, $R^2$, and $R^3$ is hydrogen. In some embodiments, all of $R^1$, $R^2$, and $R^3$ are alkyl, such as methyl.

In some embodiments, at least one of $R^4$, $R^5$, $R^6$, and $R^7$ is not hydrogen. In some embodiments, at least one of $R^4$, $R^5$, $R^6$, and $R^7$ is halo. In some embodiments, two of $R^3$, $R^4$, $R^5$, $R^6$, and $R^7$ are halo. In some embodiments, one of $R^4$, $R^5$, $R^6$, and $R^7$ is halo. In some embodiments, at least one of $R^4$, $R^5$, $R^6$, and $R^7$ is fluoro. In some embodiments, only $R^4$ is a substituent other than H and it is a hydrocarbon ring that is substituted with a halo, including, for example fluoro or chloro.

In some embodiments, any one of $R^6$ and $R^7$ or $R^5$ and $R^6$ form a phenyl ring, which is substituted or unsubstituted. In various embodiments, the phenyl ring is substituted with a halo, optionally selected from fluoro and chloro and optionally at one or more of the ortho, meta, and para positions. In various embodiments, the phenyl ring is unsubstituted.

In various embodiments, there is an optionally substituted hydrocarbon or heterocyclic ring system, e.g. a phenyl ring or naphthyl ring connected to the 5 position of the bicyclic core of Formula I (the core being the top of the structure, i.e. the tetrahydronaphthyl moiety bearing $R^5$-$R^7$ and the amino group bearing $R^1$, $R^2$ and $R^3$). In some embodiments, these phenyl or naphthyl rings are substituted with a halo, optionally selected from fluoro and chloro. In some embodiments, the halo substitution is in the ortho, meta, or para position of the phenyl or the 2, 3, 4, 5, 6, or 7 position of the naphthyl ring (where the attachment position to the compounds's core is at position 1 or 8 of the naphthyl ring). In some embodiments, the halo substitution is in the ortho of the phenyl or the 2 or 7 position of the naphthyl ring (where the attachment position to the compounds's core is at position 1 or 8 of the naphthyl ring).

In various embodiments, the total number of atoms that comprise substituents $R^4$ are at least about 5, and not more than about 20 atoms, not including hydrogen atoms (e.g. between about 5 to about 10 non-hydrogen atoms, or between about 5 to about 15 non-hydrogen atoms, or between about 10 to about 15 non-hydrogen atoms). In some embodiments, the composition is not a good substrate for one or more forms of P450 at levels administered. For instance, without wishing to be bound by theory, larger numbers of non-hydrogen atoms that comprise substituents $R^4$ may prevent metabolism associated with P450 (such metabolism may be, without wishing to be bound by theory, oxidation-mediated). For example, in some embodiments, the composition is not a substrate for one or more families of P450 (e.g. CYP1, CYP2, CYP3, CYP4, CYP5, CYP7, CYP8, CYP11, CYP17, CYP19, CYP20, CYP21, CYP24, CYP26, CYP27, CYP39, CYP46, and CYP51). In some embodiments, the composition is not a substrate for one or more of CYP1A2, CYP2C19, CYP2C9, CYP2D6, CYP2E1, and CYP3A4. In these embodiments, the compound is suited for avoiding P450-mediated reduction in a pharmacological effect.

In various embodiments, the compound or composition is a derivative any one of the 4-PAT or 5-PAT genera or species found in International Patent Publication Nos. WO 2008/156707, WO 2008/154044, WO 2009/061436, and WO 2010/129048, and International Patent Application No. PCT/US2015/031523, the contents of which are hereby incorporated by reference in their entireties. In various embodiments, the derivitization is at the nitrogen attached to position 2 of the compound or composition's tetrahydronaphthyl (tetralin) core. For clarity, the tetrahydronaphthyl core is shown below and position 2 bears an amino group:

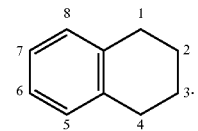

In Formula I or Formula II herein, this amino group at position 2 is denoted as bearing $R^1$, $R^2$, and $R^3$. Accordingly, in various embodiments, any of the compounds of the above incorporated documents bear an amino group at position 2 and the amino group bears three of any of the substituents described herein to provide a net positive charge e.g. a quaternary ammonium. For example, any of the 4-PAT or 5-PAT compounds in the above incorporated documents are derivatized to comprise an amino group at position 2 that bears three alkyl substituents (e.g. three methyl substituents).

For clarity, with reference to WO 2008/156707, the present compounds and compositions include derivatives at position $R_1$ of formula (I) therein, which is a genus of 4-PAT compounds. For instance, $R_1$ of formula (I) of WO 2008/156707, as well as compounds PAT #1-31 (e.g. page 21 of WO 2008/156707, the contents of which are hereby incorporated by reference in their entirety) is, in the present invention, an amino group bearing three substituents described herein (e.g. three methyl groups) and therefore a positive charge. In some embodiments, such compounds may agonize 5-$HT_{2c}$. In some embodiments, such compounds may antagonize 5-$HT_{2a}$ and/or 5-$HT_{2b}$.

Further, with reference to WO 2008/154044, the present compounds and compositions include derivatives at the amino group of position 2 of formula (I) therein, which is a genus of 5-PAT compounds (see pages 3-5 and FIG. 1 of WO 2008/154044, the contents of which are hereby incorporated by reference in their entirety). For instance, the amino group of position 2 of formula (I) of WO 2008/154044, as well as compounds PAT #32-40 (e.g. page 16 of 2008/154044, the contents of which are hereby incorporated by reference in their entirety) is, in the present invention, an amino group bearing three substituents described herein (e.g. three methyl groups) and therefore a positive charge. In some embodiments, such compounds may agonize 5-$HT_{2c}$. In some embodiments, such compounds may antagonize 5-$HT_{2a}$ and/or 5-$HT_{2b}$.

Further still, with reference to WO 2009/061436, the present compounds and compositions include derivatives at the amino group of position 2 ($R_1$) of the 4-PAT compounds therein (see Table 1-3, pages 15-16, compounds PAT #1-40 and 41(a)-(p), the contents of which are hereby incorporated by reference in their entirety). For instance, the amino group of the compounds of Table 1-3 (or $R_1$) is, in the present invention, an amino group bearing three substituents described herein (e.g. three methyl groups) and therefore a positive charge.

Further still, with reference to WO 2010/129048, the present compounds and compositions include derivatives at position $R_1$ of any of formulae (I)-(VI) therein, which are genera of 4-PAT compounds. For instance, $R_1$ of any of formulae (I)-(VI) of WO 2010/129048, compounds of Tables 1-3 therein (e.g. pages 31-35 of WO 2010/129048, the contents of which are hereby incorporated by reference in their entirety), and compounds formed by adding the groups of Table 7 e.g. at the 4- or 5-position of the tetrahydronaphthyl core (Table 7, pages 70-89 of WO 2010/129048 is hereby incorporated by reference in its entirety), is, in the present invention, an amino group bearing three substituents described herein (e.g. three methyl groups) and therefore a positive charge. In some embodiments, such compounds may agonize 5-HT$_{2c}$. In some embodiments, such compounds may antagonize 5-HT$_{2a}$ and/or 5-HT$_{2b}$.

Further still, with reference to WO 2010/129048, the present compounds and compositions include derivatives at position R$_1$ of formula (V) therein, which is a genus of 5-PAT compounds. For instance, R$_1$ of formula (V) of WO 2010/129048, the 5-PAT compounds of Table 3 (e.g. page 35 of WO 2010/129048, the contents of which are hereby incorporated by reference in their entirety) and compounds formed by adding the groups of Table 7 e.g. at the 4- or 5-position of the tetrahydronaphthyl core (Table 7, pages 70-89 of WO 2010/129048 is hereby incorporated by reference in its entirety), is, in the present invention, an amino group bearing three substituents described herein (e.g. three methyl groups) and therefore a positive charge. In some embodiments, such compounds may agonize 5-HT$_{2c}$. In some embodiments, such compounds may antagonize 5-HT$_{2a}$ and/or 5-HT$_{2b}$.

Further still, with reference to International Patent Application No. PCT/US2015/031523, the present compounds and compositions include, with reference to Formula (I') therein, instances in which all of R$_1$ to R$_3$ are identical e.g. bearing the substituents described herein (e.g. three methyl groups) and therefore have a positive charge or, with reference to Formula (I) therein, the amino group at position 2 bears a further substituent in addition to R$^1$ and R$^2$, the additional substituent and R$^1$ and R$^2$ being substituents described herein (e.g. three methyl groups) and therefore having a positive charge.

In some embodiments, the compound or composition is

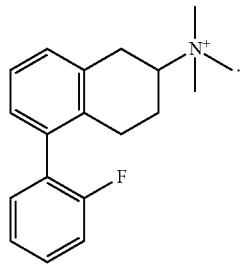 [SMILES: C[N+](C)(C)C1CCc2c(cccc2-c2ccccc2F)C1]

In some embodiments, the compound or composition is the (+) enantiomer of the above compound.

In some embodiments, the compound or composition is:

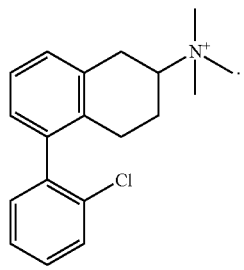 [SMILES: C[N+](C)(C)C1CCc2c(cccc2-c2ccccc2Cl)C1]

In some embodiments the compound or composition is the (+) enantiomer of the above compound.

In some embodiments, the compound or composition is

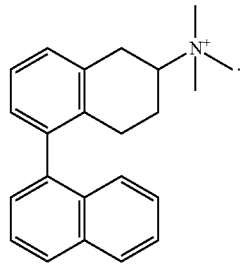 [SMILES: C[N+](C)(C)C1CCc2c(cccc2-c2cccc3ccccc23)C1]

In some embodiments, the compound or composition is the (−) enantiomer of the above compound.

In various embodiments, the compound or composition may be any one of:

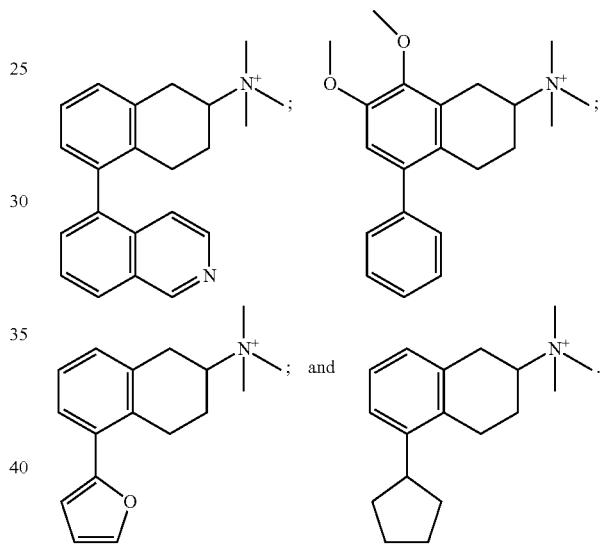

In some embodiments, the compound or composition is the (−) or (+) enantiomer of any of the above compounds.

In various embodiments, the compositions of the present invention comprise at least about 70%, or at least about 80%, or at least about 85%, or at least about 90%, or at least about 95%, or at least about 97%, or at least about 99% of a single enantiomer. In various embodiments, a least about 85%, or at least about 90%, or at least about 95%, or at least about 97%, or at least about 99% of a single enantiomer.

In some embodiments, the compositions of the present invention comprises less than about 30%, or less than about 20%, or less than about 15%, or less than about 10%, or less than about 5%, or less than about 3%, or less than about 1% of a single enantiomer.

In some embodiments, the present compounds and compositions are substantially in the form of a single enantiomer and essentially free of the corresponding enantiomer.

In some embodiments, a single enantiomer has functional properties (e.g. serotonin receptor selectivity) that are not found in a corresponding enantiomer. For example, in some embodiments, the (+) enantiomer has serotonin-receptor modulating properties that are not found in the corresponding (−) enantiomer (e.g. the (−) enantiomer does not bind or modulate one of more serotonin receptors at physiological levels). By way of further example, in some embodiments, the (−) enantiomer has serotonin-receptor modulating properties that are not found in the corresponding (+) enantiomer (e.g. the (+) enantiomer does not bind or modulate one of more serotonin receptors at physiological levels). Such a stereoselectivity, in some embodiments, also applies to (R)- and (S)- and d- and l-. Accordingly, in some embodiments, the invention does not provide racemates or racemic mixtures. In some embodiments, the present compounds and compositions find use as entiopure drugs.

In various embodiments, the present invention requires separation of a racemate into its components, the pure enantiomers, i.e. chiral resolution. Techniques to achieve substantially enantiomerically pure compounds are known and include, by way of non-limiting example, crystallization, chromatography (e.g. HPLC), and enzymatic resolution. Various techniques for chiral resolution are found in Proter *Pure Appl. Chem.* 63 (8): 1119-1122, the contents of which are hereby incorporated by reference in their entirety. In various embodiments, measurement of the Eudysmic ratio may assist in determining the final properties of the composition. For example, one enantiomer is the eutomer while the other enantiomer is the distomer and comparison of two may involve the quotient of activity or binding measurements (e.g. $EC_{50}$ or $IC_{50}$).

In further embodiments, the present compounds and compositions are entiopure drugs. However, in instances in which corresponding enantiomers provide different but desirable properties (e.g. physiologically relevant modulation at different serotonin receptors), such enantiomers may be combined as a combination composition of known amounts.

In various embodiments, the present compounds or compositions modulate one or more serotonin receptors. For example, one or more of 5-$HT_1$ receptors (e.g. one or more of 5-$HT_{1A}$, 5-$HT_{1B}$, 5-$HT_{1C}$, 5-$HT_{1D}$, 5-$HT_{1E}$, 5-$HT_{1F}$); 5-$HT_2$ receptors (e.g. one or more of 5-$HT_{2A}$, 5-$HT_{2B}$, 5-$HT_{2C}$); 5-$HT_3$ receptors; 5-$HT_4$ receptors; 5-$HT_5$ receptors (e.g. 5-$HT_{5A}$); 5-$HT_6$ receptors; and 5-$HT_7$ receptors may be modulated. In various embodiments, the present compounds or compositions bind one or more serotonin receptors with a binding affinity ($K_i$) of less than about 100 nM, or less than about 50 nM, or less than about 25 nM, or less than about 20 nM, or less than about 10 nM, or less than about 5 nM, or less than about 2 nM, or less than about 1 nM. In various embodiments, the present compounds or compositions bind one or more serotonin receptors with a binding affinity ($K_i$) of about 100 nM, or about 90 nM, or about 80 nM, or about 75 nM, or about 70 nM, or about 60 nM, or about 50 nM, or about 40 nM, or about 30 nM, or about 25 nM, or about 20 nM, or about 10 nM, or about 5 nM, or about 4 nM, or about 3 nM, or about 2 nM, or about 1 nM.

In various embodiments, the present compounds or compositions may be full agonist, partial agonist, antagonist, inverse agonist, etc. at one or more receptors described herein (e.g. one or more serotonin receptors). In some embodiments, the invention provides for partial agonists at one or more receptors described herein (e.g. one or more serotonin receptors) specifically. In some embodiments, the present compounds or compositions are not full agonists at one or more receptors described herein (e.g. one or more serotonin receptors). In some embodiments, such partial agonism may provide constant, weak level of activity at the receptor, as compared to a full agonist. Further, without wishing to be bound by theory, such partial agonism may prevent adaptive regulatory mechanisms that may develop after repeated exposure to potent full agonists or antagonists. Further, in embodiments relating to serotonin receptor modulation, partial agonism of the present compounds or compositions may reduce or eliminate the risk of serotonin syndrome (e.g., fever, cardiac arrhythmia, seizures, loss of consciousness). For example, some 5-$HT_1$ agonists (e.g. triptans) are known to cause serotonin syndrome. Partial agonism is believed to avoid this deleterious side effect.

In various embodiments, the present compound or composition binds to one or more of the serotonin 5-$HT_7$ and 5-$HT_{1A}$ receptor at physiologically relevant levels. In various embodiments, the present compound or composition is a dual agonist of the serotonin 5-$HT_7$ and 5-$HT_{1A}$ receptors. In various embodiments, the present compound or composition binds to the serotonin 5-$HT_7$ receptor with a binding affinity ($K_i$) of less than about 100 nM, or less than about 50 nM, or less than about 25 nM, or less than about 20 nM, or less than about 10 nM, or less than about 5 nM, or less than about 2 nM, or less than about 1 nM. In various embodiments, the present compound or composition binds to the serotonin 5-$HT_7$ receptor with a binding affinity ($K_i$) of about 100 nM, or about 90 nM, or about 80 nM, or about 75 nM, or about 70 nM, or about 60 nM, or about 50 nM, or about 40 nM, or about 30 nM, or about 25 nM, or about 20 nM, or about 10 nM, or about 5 nM, or about 4 nM, or about 3 nM, or about 2 nM, or about 1 nM. In various embodiments, the present compound or composition binds to the serotonin 5-$HT_{1A}$ receptor with a binding affinity ($K_i$) of less than about 100 nM, or less than about 50 nM, or less than about 25 nM, or less than about 20 nM, or less than about 10 nM, or less than about 5 nM, or less than about 2 nM, or less than about 1 nM. In various embodiments, the present compound or composition binds to the serotonin 5-$HT_{1A}$ receptor with a binding affinity ($K_i$) of about 100 nM, or about 90 nM, or about 80 nM, or about 75 nM, or about 70 nM, or about 60 nM, or about 50 nM, or about 40 nM, or about 30 nM, or about 25 nM, or about 20 nM, or about 10 nM, or about 5 nM, or about 4 nM, or about 3 nM, or about 2 nM, or about 1 nM.

In various embodiments, the present compound or composition does not bind or modulate one or more of the serotonin 5-$HT_{2A}$ and 5-$HT_{2C}$ receptors at physiologically-relevant levels. In various embodiments, the present compound or composition binds one or more of the serotonin 5-$HT_{2A}$ and 5-$HT_{2C}$ receptors with an affinity of greater than about 300 nM, or greater than about 400 nM, or greater than about 500 nM, or greater than about 750 nM, or greater than about 1 µM. In some embodiments, the present compound or composition binds one or more of the serotonin 5-$HT_{2A}$ and 5-$HT_{2C}$ receptors with an affinity of about 10 µM, or about 5 µM, or about 1 µM, or about 900 nM, or about 800 nM, or about 750 nM, or about 700 nM, or about 600 nM, or about 500 nM, or about 400 nM, or about 250 nM.

Accordingly, in some embodiments, the present compound or composition selectively binds to serotonin 5-$HT_7$ and 5-$HT_{1A}$ receptors over other serotonin receptors. In various embodiments, the present compound or composition binds one or more of the serotonin 5-$HT_7$ and 5-$HT_{1A}$ receptors with at least about 10-fold, or at least about 20-fold, or at least about 30-fold, or at least about 40-fold, or at least about 50-fold, or at least about 75-fold, or at least about 100-fold higher affinity than one or more of the serotonin 5-$HT_{2A}$ and 5-$HT_{2C}$ receptors. In various embodiments, the present compound or composition binds one or more of the serotonin 5-$HT_7$ and 5-$HT_{1A}$ receptors with about a 10-fold, or 20-fold, or 25-fold, or 30-fold, or 40-fold, or 50-fold, or 60-fold, or 70-fold, or 75-fold, or 80-fold, or 90-fold, or 100-fold higher affinity than one or more of the serotonin 5-HT$_{2A}$ and 5-HT$_{2C}$ receptors.

In various embodiments, the present compound or composition binds to one or more of the 5-HT$_{2a}$, 5-HT$_{2b}$, and 5-HT$_{2c}$ receptors at physiologically relevant levels. In various embodiments, the present compound or composition binds to the one or more of the 5-HT$_{2a}$, 5-HT$_{2b}$, and 5-HT$_{2c}$ receptor with a binding affinity ($K_i$) of less than about 100 nM, or less than about 50 nM, or less than about 25 nM, or less than about 20 nM, or less than about 10 nM, or less than about 5 nM, or less than about 2 nM, or less than about 1 nM. In various embodiments, the present compound or composition binds to the one or more of the 5-HT$_{2a}$, 5-HT$_{2b}$, and 5-HT$_{2c}$ receptor with a binding affinity ($K_i$) of about 100 nM, or about 90 nM, or about 80 nM, or about 75 nM, or about 70 nM, or about 60 nM, or about 50 nM, or about 40 nM, or about 30 nM, or about 25 nM, or about 20 nM, or about 10 nM, or about 5 nM, or about 4 nM, or about 3 nM, or about 2 nM, or about 1 nM. In various embodiments, the present compound or composition selectively binds the serotonin 5-HT$_{2c}$ receptor 5-HT$_{2A}$ relative to 5-HT$_{2a}$ or 5-HT$_{2b}$.

In some embodiments, the selective binding to certain serotonin receptors over other serotonin receptors (e.g. a preference for 5-HT$_7$ and 5-HT$_{1A}$ receptors) is enantiomer-mediated. That is, in some embodiments, one enantiomer of a compound displays the selectively binding while the other does not. For example, in some embodiments, the present compound or composition binds one or more of the serotonin 5-HT$_7$ and 5-HT$_{1A}$ receptors with an at least about 10-fold, or at least about 20-fold, or at least about 30-fold, or at least about 40-fold, or at least about 50-fold, or at least about 75-fold, or at least about 100-fold higher affinity than a corresponding enantiomer. In some embodiments, the present compound or composition binds one or more of the serotonin 5-HT$_7$ and 5-HT$_{1A}$ receptors with about 10-fold, or about 20-fold, or about 30-fold, or about 40-fold, or about 50-fold, or about 75-fold, or about 100-fold higher affinity than a corresponding enantiomer.

In various embodiments, the present compound or composition does not bind or modulate one or more of the histamine H1 receptor, dopamine D2, and adrenergic $\alpha_{1A}$ and $\alpha_{1B}$ receptors at physiologically-relevant levels.

In various embodiments, the present compound or composition binds one or more of the histamine H1 receptor, dopamine D2, and adrenergic $\alpha_{1A}$ and $\alpha_{1B}$ receptors with an affinity of greater than greater than about 500 nM, or greater than about 750 nM, or greater than about 1 μM. In various embodiments, the present compound or composition binds one or more of the histamine H1 receptor, dopamine D2, and adrenergic $\alpha_{1A}$ and $\alpha_{1B}$ receptors with an affinity of 10 μM, or about 5 μM, or about 1 μM, or about 900 nM, or about 800 nM, or about 750 nM, or about 700 nM, or about 600 nM, or about 500 nM, or about 400 nM, or about 250 nM.

Accordingly, in some embodiments, the present compound or composition selectively binds one or more serotonin receptor over one or more of the histamine H1 receptor, dopamine D2, and adrenergic $\alpha_{1A}$ and $\alpha_{1B}$ receptors. In various embodiments, the present compound or composition binds one or more serotonin receptor with at least about 10-fold, or at least about 20-fold, or at least about 30-fold, or at least about 40-fold, or at least about 50-fold, or at least about 75-fold, or at least about 100-fold higher affinity than one or more of the histamine H1 receptor, dopamine D2, and adrenergic $\alpha_{1A}$ and $\alpha_{1B}$ receptors. In various embodiments, the present compound or composition binds one or more serotonin receptor with about a 10-fold, or 20-fold, or 25-fold, or 30-fold, or 40-fold, or 50-fold, or 60-fold, or 70-fold, or 75-fold, or 80-fold, or 90-fold, or 100-fold higher affinity than one or more of the histamine H1 receptor, dopamine D2, and adrenergic $\alpha_{1A}$ and $\alpha_{1B}$ receptors.

In various aspects, the present invention relates to a compound or pharmaceutical composition of the structure represented by Formula (Ia):

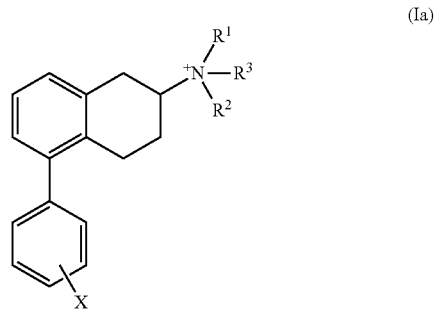

(Ia)

or pharmaceutically acceptable salt thereof, where each of $R^1$, $R^2$, and $R^3$ are defined as above for Formula I and X is independently hydrogen, alkyl, aryl, halo, nitro, amino, heteroaryl, cycloalkyl, heterocyclic, or alkoxy.

In some embodiments, the compound is the (+) enantiomer. In some embodiments, the compound is the (−) enantiomer.

In some embodiments, each of $R^1$, $R^2$, and $R^3$ is independently hydrogen, alkyl, aryl, halo, nitro, amino, heteroaryl, cycloalkyl, heterocyclic, or alkoxy. In some embodiments, $R^1$, $R^2$, and $R^3$ are identical. In some embodiments, $R^1$, $R^2$, and $R^3$ are methyl.

In some embodiments, X is a halo. In some embodiments, X is fluoro. In some embodiments, X is chloro. In some embodiments, X is bromo. In some embodiments, X is iodo. In some embodiments, X is in the ortho position. In some embodiments, X is in the meta position. In some embodiments, X is in the para position.

In some embodiments, the compound of Formula Ia is enantiomerically pure. In some embodiments, the compound of Formula Ia is substantially the (+) enantiomer. In some embodiments, the compound of Formula Ia is substantially devoid of the (+) enantiomer. In some embodiments, the compound of Formula Ia is substantially the (−) enantiomer. In some embodiments, the compound of Formula Ia is substantially devoid of the (−) enantiomer.

In some embodiments, the compounds and compositions of the present invention may take the form of a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In some embodiments, the compounds and compositions of the present invention can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water, saline solutions and aqueous dextrose and glycerol solutions can also be employed as liquid excipients. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

The compounds and compositions of the present invention can be present in various formulations. Any compound and composition (and/or additional agents) described herein can take the form of solutions, suspensions, emulsion, drops, tablets, pills, pellets, capsules, capsules containing liquids, powders, sustained-release formulations, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the compounds and compositions can also include a solubilizing agent. Also, the compounds and compositions can be delivered with a suitable vehicle or delivery device as known in the art. Combination therapies outlined herein can be co-delivered in a single delivery vehicle or delivery device.

The formulations comprising the compounds and compositions of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In some embodiments, the administering is effected orally. In some embodiments, the administering is by absorption through epithelial or mucocutaneous linings (e.g., oral mucosa). Various delivery systems are known, e.g., encapsulation in liposomes, microparticles, microcapsules, capsules, etc., and can be used to administer. In various embodiments, the compounds and compositions of the present invention are formulated to be suitable for oral delivery. In various embodiments, the compounds and compositions of the present invention are formulated to be suitable for transmucosal delivery (see, e.g. Msatheesh, et al. Expert Opin Drug Deliv. 2012 June; 9(6):629-47, the entire contents of which are hereby incorporated by reference).

Compositions or compounds for oral delivery can be in the form of tablets, lozenges, aqueous or oily suspensions, granules, powders, emulsions, capsules, syrups, or elixirs, for example. In some embodiments, the compounds and compositions of the present invention are in the form of a capsule, tablet, patch, or lozenge. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically capsule containing a driving compound capable of active driving any compound or composition described herein is also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the compounds and compositions of the present invention, or formulations thereof, do not substantially accumulate in the brain. In various embodiments, the compounds and compositions, or formulations thereof, deliver a physiological amount of present compound or composition to the periphery for at least about 6 hours, or at least about 9 hours, or at least about 12 hours, or at least about 15 hours, or at least about 18 hours, or at least about 21 hours, or at least about 24 hours. In various embodiments, the compounds and compositions, or formulations thereof, deliver a physiological amount of present compound or composition to the periphery for about 6 hours, or about 9 hours, or about 12 hours, or about 15 hours, or about 18 hours, or about 21 hours, or about 24 hours.

Further, the present compounds or compositions may find use as a combination therapy or co-formulation with one or more additional therapeutic agents. For example, such additional therapeutic agents can include an anti-bacterial agent, which includes, but is not limited to, cephalosporin antibiotics (e.g. cephalexin, cefuroxime, cefadroxil, cefazolin, cephalothin, cefaclor, cefamandole, cefoxitin, cefprozil, and ceftobiprole); fluoroquinolone antibiotics (e.g. cipro, Levaquin, floxin, tequin, avelox, and norflox); tetracycline antibiotics (e.g. tetracycline, minocycline, oxytetracycline, and doxycycline); penicillin antibiotics (e.g. amoxicillin, ampicillin, penicillin V, dicloxacillin, carbenicillin, vancomycin, and methicillin); monobactam antibiotics (e.g. aztreonam); and carbapenem antibiotics (e.g. ertapenem, doripenem, imipenem/cilastatin, and meropenem). In some embodiments, the additional therapeutic agent is metronidazole (e.g. FLAGYL), fidaxomicin (e.g. DIFICID), or vancomycin (e.g. VANCOCIN), rifaximin, charcoal-based binders/adsorbents (e.g. DAV132), fecal bacteriotherapy, probiotic therapy (see, e.g., *Intnat'l J Inf Dis,* 16 (11): e786, the contents of which are hereby incorporated by reference). In some embodiments, the additional therapeutic agent is an antidiarrheal agent, which include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents. In some embodiments, the additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art.

Any compound or composition (and/or additional therapeutic agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

Administration of any compounds or compositions (and/or additional agents) described herein can, independently, be one to four times daily. Administration can be for the duration of one day or one month, two months, three months, six months, one year, two years, three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

The present compounds and compositions also find use in various therapeutic methods.

In some aspects, the present invention relates to method for treating or preventing a gastrointestinal disorder or condition, optionally selected from inflammatory bowel disease, irritable bowel syndrome, celiac disease, and an enteric infection, comprising administering the compound or composition described herein to a patient in need thereof.

In some aspects, the present invention relates to a method for treating or preventing a functional GI disorder comprising administering the composition described herein to a patient in need thereof.

Illustrative gastrointestinal disorders or conditions include, but are not limited to, hyperproliferative diseases, for example, carcinomas (e.g., colorectal cancer); autoimmune and inflammatory bowel diseases (IBD), for example, Celiac's disease, Crohn's disease, and colitis (e.g., ulcerative colitis); irritable bowel syndrome; infectious diseases of the intestine, for example, *C. difficile* infection (CDI) and/or a *C. difficile*-associated disease, pseudomembranous colitis, amebiasis or intestinal tuberculosis; parasitic disorders, colonic polyps; cysts; diverticular disease (e.g., diverticulosis, diverticulitis, and diverticular bleeding); constipation; intestinal obstruction; malabsorption syndromes; rectal diseases; ulceration of the mucosa; intestinal dysbiosis (e.g., intestinal bacteria overgrowth); dyspepsia; gastroesophageal reflux disease; gastroparesis; nausea; vomiting; and diarrhea. Additional diseases, disorders and conditions which are suitable for treatment with the compositions and methods of the invention include those listed in Table 3 of WO 2014/121298, the entire contents of which are incorporated herein by reference.

In some embodiments, the present invention provides methods for treating or preventing autoimmune and inflammatory bowel diseases (IBD), for example, Celiac's disease, Crohn's disease, and colitis (e.g., ulcerative colitis), comprising administering an effective amount of a pharmaceutical composition and/or formulation (and/or additional therapeutic agent) described herein to a subject or a patient need thereof.

In some embodiments, the present invention provides methods for treating or preventing irritable bowel syndrome (IBS), comprising administering an effective amount of a pharmaceutical composition and/or formulation (and/or additional therapeutic agent) described herein to a subject or a patient need thereof. In an embodiment, the IBS is IBS with constipation (IBS-C). In an embodiment, the IBS is IBS with diarrhea (IBS-D). In an embodiment, the IBS is mixed IBS (IBS-M).

In some embodiments, methods of the invention are useful for treating constipation, dyspepsia, gastroesophageal reflux disease, gastroparesis, nausea, vomiting, diarrhea, and a diverticular disease (e.g., diverticulosis, diverticulitis, and diverticular bleeding).

In some aspects, the present invention relates to method for modulating a serotonin receptor in the GI tract, comprising administering the compound or composition described herein to a patient in need thereof.

In some aspects, the present invention relates to a method for treating or preventing a cardiopulmonary disorder comprising administering the composition described herein to a patient in need thereof.

Illustrative cardiopulmonary disorders include cardiac valvulopathy and pulmonary hypertension. Cardiopulmonary disorders include right-sided and/or left-sided cardiac fibrosis, inclusive of cardiomyopathy and congestive heart failure. Also included are ventricular tachyarrhythmia, left ventricular (LV) dysfunction, and heart failure, as well as right ventricular failure (RVF) and left ventricular failure (LVF). A further cardiopulmonary disorder is heart valve disease, which includes left heart diseases (e.g. diseases of the aortic valve (e.g. aortic valve stenosis, aortic valve insufficiency, aortic valve incompetence, aortic valve regurgitation) and/or the mitral valve (e.g. mitral valve stenosis, mitral valve insufficiency, mitral valve incompetence, mitral valve regurgitation) and/or right heart diseases (e.g. diseases of the tricuspidvalve (e.g. tricuspid valve stenosis, tricuspid valve insufficiency, tricuspid valve incompetence, tricuspid valve regurgitation) and/or the pulmonary valve (e.g. pulmonary valve stenosis, pulmonary valve insufficiency, pulmonary valve incompetence, pulmonary valve regurgitation). Further, cardiopulmonary disorders are heart valve dysplasia; tetralogy of Fallot, Ebstein's anomaly, cardiomyopathies (including, for example, dilated cardiomyopathy, restrictive cardiomyopathy and hypertrophic cardiomyopathy), elevated heart rate, vasoconstriction, and heart failure.

In various embodiments, e.g. those pertaining to treating or preventing a cardiopulmonary disorder, combination therapy or co-formulation with an additional therapeutic agent may be provided. Illustrative additional therapeutic agents include: anticoagulents (e.g. dalteparin (FRAGMIN), danaparoid (ORGARAN), enoxaparin (LOVENOX), heparin, tinzaparin (INNOHEP), and warfarin (COUMADIN)); Antiplatelet Agents (e.g. aspirin, ticlopidine, clopidogrel, and dipyridamole); ACE Inhibitors (e.g. benazepril (LOTENSIN), captopril (CAPOTEN), enalapril (VASOTEC), fosinopril (MONOPRIL), lisinopril (PRINIVIL, ZESTRIL), moexipril (UNIVASC), perindopril (ACEON), quinapril (ACCUPRIL), ramipril (ALTACE) and, trandolapril (MAVIK)); Angiotensin II Receptor Blockers (or Inhibitors) (e.g. candesartan (ATACAND), eprosartan (TEVETEN), irbesartan (AVAPRO), losartan (COZAAR), telmisartan (MICARDIS) and, valsartan (DIOVAN)); beta-blockers (e.g. acebutolol (SECTRAL), atenolol (TENORMIN), betaxolol (KERLONE), bisoprolol/hydrochlorothiazide (ZIAC), bisoprolol (ZEBETA), carteolol (CARTROL), metoprolol (LOPRESSOR, TOPROL XL), nadolol (CORGARD), propranolol (INDERAL), sotalol (BETAPACE) and, timolol (BLOCADREN)); calcium channel blockers (e.g. amlodipine (NORVASC, LOTREL), bepridil (VASCOR), diltiazem (CARDIZEM, TIAZAC), felodipine (PLENDIL), nifedipine (ADALAT, PROCARDIA), nimodipine (NIMOTOP), nisoldipine (SULAR), and verapamil (CALAN, ISOPTIN, VERELAN); diuretics (e.g. amiloride (MIDAMOR), bumetanide (BUMEX), chlorothiazide (DIURIL), chlorthalidone (HYGROTON), furosemide (LASIX), hydrochlorothiazide (ESIDRIX, HYDRODIURIL), indapamide (LOZOL), and Spironolactone (ALDACTONE); vasodilators (e.g. isosorbide dinitrate (ISORDIL), nesiritide (NATRECOR), hydralazine (APRESOLINE), nitrates and minoxidil); digitalis preparations (e.g. lanoxin); and statins (e.g., atorvastatin, pravastatin, fluvastatin).

Definitions

The term "acyl" means both substituents of the formula Rx-C(O)—, where Rx is alkyl, heteroalkyl, alkenyl, alkynyl, cycloalkyl, heterocycloalkyl, aryl, arylalkyl, heteroaryl, and heteroarylalkyl.

The term "alkyl" means both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonate, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively. In some embodiments, the alkyl group may have from 1 to 12 carbon atoms, e.g. about 1 carbon atom, or about 2 carbon atoms, or about 3 carbon atoms, or about 4 carbon atoms, or about 5 carbon atoms, or about 6 carbon atoms, or about 7 carbon atoms, or about 8 carbon atoms, or about 9 carbon atoms, or about 10 carbon atoms, or about 11 carbon atoms, or about 12 carbon atoms. Illustrative alkyl groups include methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms. Illustrative alkoxy substituents include, but are not limited to, methoxy, ethoxy, propoxy, isopropoxy, cyclopropyloxy and cyclohexyloxy. In some embodiments, the alkoxy is a lower alkoxy (containing one to six carbon atoms). The alkoxy substituent is optionally substituted.

The terms "alkenyl" and "alkynyl" refer to unsaturated aliphatic groups analogous in length and possible substitution to the alkyls described above, but that contain at least one double or triple bond, respectively. In some embodiments, the "alkenyl" or "alkynyl" group may have from 2 to 12 carbon atoms, e.g. about 2 carbon atoms, or about 3 carbon atoms, or about 4 carbon atoms, or about 5 carbon atoms, or about 6 carbon atoms, or about 7 carbon atoms, or about 8 carbon atoms, or about 9 carbon atoms, or about 10 carbon atoms, or about 11 carbon atoms, or about 12 carbon atoms.

Amino or "amine" substituents include those of the formula —N($R_b$)$_2$, where $R_b$ is hydrogen, alkyl, (halo)alkyl, alkenyl, alkynyl, carbocyclyl, carbocyclylalkyl, aryl, aralkyl, heterocycloalkyl, heterocycloalkylalkyl, heteroaryl heteroarylalkyl, or other substituent described herein. When —N($R_b$)$^2$ has two $R_b$ substituents other than hydrogen, they can be combined with the nitrogen atom to form a 4-, 5-, 6- or 7-membered ring. For example, —N($R_b$)$^2$ is intended to include, for example, pyrrolidinyl and morpholinyl.

Amide or "amido" substituents include those of the formula —C(O)N($R_y$)$_2$ or —NHC(O)$R_y$, where $R_y$ is selected from the group consisting of hydrogen, alkyl, alkenyl, alkynyl, carbocyclyl, carbocyclylalkyl, cycloalkyl, aryl, heteroaryl, or other substituent described herein. The $R^y$ of —$N(R_y)_2$ of the amide may optionally be taken together with the nitrogen to which it is attached to form a 4-, 5-, 6- or 7-membered ring.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "halogen" and "halo" designate fluoro, chloro, bromo or iodo. Thus, substituents include, without limitation, haloalkyl, haloalkenyl, haloalkynyl and haloalkoxy.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The terms "heterocyclic" or "heterocyclo" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring, which typically contains from 3 to 14 ring atoms, from 3 to 8 ring atoms, from 3 to 6 ring atoms, or from 5 to 6 ring atoms. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, anthracene, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The term "heteroatom" as used herein means an atom of any element other than carbon or hydrogen. Preferred heteroatoms are nitrogen, oxygen, sulfur and phosphorus.

The term "hydroxyl" means —OH.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, the group substituents described above and for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_1$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —$CONH_2$, mono- or di-($C_1$-$C_8$alkyl)aminocarbonyl, —$SO_2NH_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

"Substituted" means having substituents replacing an atom and includes one or more of halo, acyl, acyloxy, alkyl, heteroalkyl, alkenyl, heteroalkenyl, alkynyl, heteroalkynyl, alkoxy, alkoxycarbonyl, cycloalkyl, heterocycloalkyl, aryl, arylalkyl, heteroaryl, heteroarylalkyl, hydroxy, cyano, trifluoromethyl, trifluoromethoxy, nitro, and trimethylsilanyl, ether, ester, sulfide, disulfide, sulfonyl, sulfinyl, sulfonamidyl, sulfonate, sulfoxyl, phosphate ester, phosphine, borate ester, carbonyl, carboxylate, carbamate, amine, imide, and quinidine. Such substituents can also include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonate, sulfamoyl, sulfonamido, nitro, trifluoromethyl, cyano, azido, heterocyclyl, alkylaryl, or an aromatic or heteroaromatic moiety.

The term "sulfhydryl" or "thiol" means —SH.

The term "treat" or "treatment" means any degree of reduction of symptoms or causation of a disease or medical condition. The term "prevent" or "prevention" means any degree of avoiding the onset or acquisition of a disease or medical condition.

As used herein, "consisting essentially of" allows the inclusion of materials or steps that do not materially affect the basic and novel characteristics of the claim. Any recitation herein of the term "comprising" can be exchanged with "consisting essentially of" or "consisting of".

This invention is further illustrated by the following non-limiting examples.

EXAMPLES

Example 1: 5-PAT Synthesis

Synthesis of compounds described herein is shown in Scheme 1, which involves 6-steps. Briefly, 5-Br-tetralone (1), obtained by reacting 1-tetralone with bromine/AlCl$_3$, enylphosphine Pd [0], the mixture was degassed, and the 2'-F- or 2'-Cl-phenylboronic acid was added. The reaction mixture was stirred at 80° C. for 3 h and then cooled to room temperature before adding H$_2$O$_2$ to quench excess boronic acid to obtain the 5-(2'-F- or 2'-Cl)-phenyl-2-tetralones (7). Reductive amination with dimethylamine gave 5-(2'[o]-F or Cl)-phenyl-2-dimethylaminotetralin racemates (8), resolved by polysaccharide-based chiral stationary phase (CSP)-HPLC to obtain 25 mg each (2R) and (2S)-o-F-PAT and -o-Cl-5-PAT. Other compounds synthesized herein involve this general process.

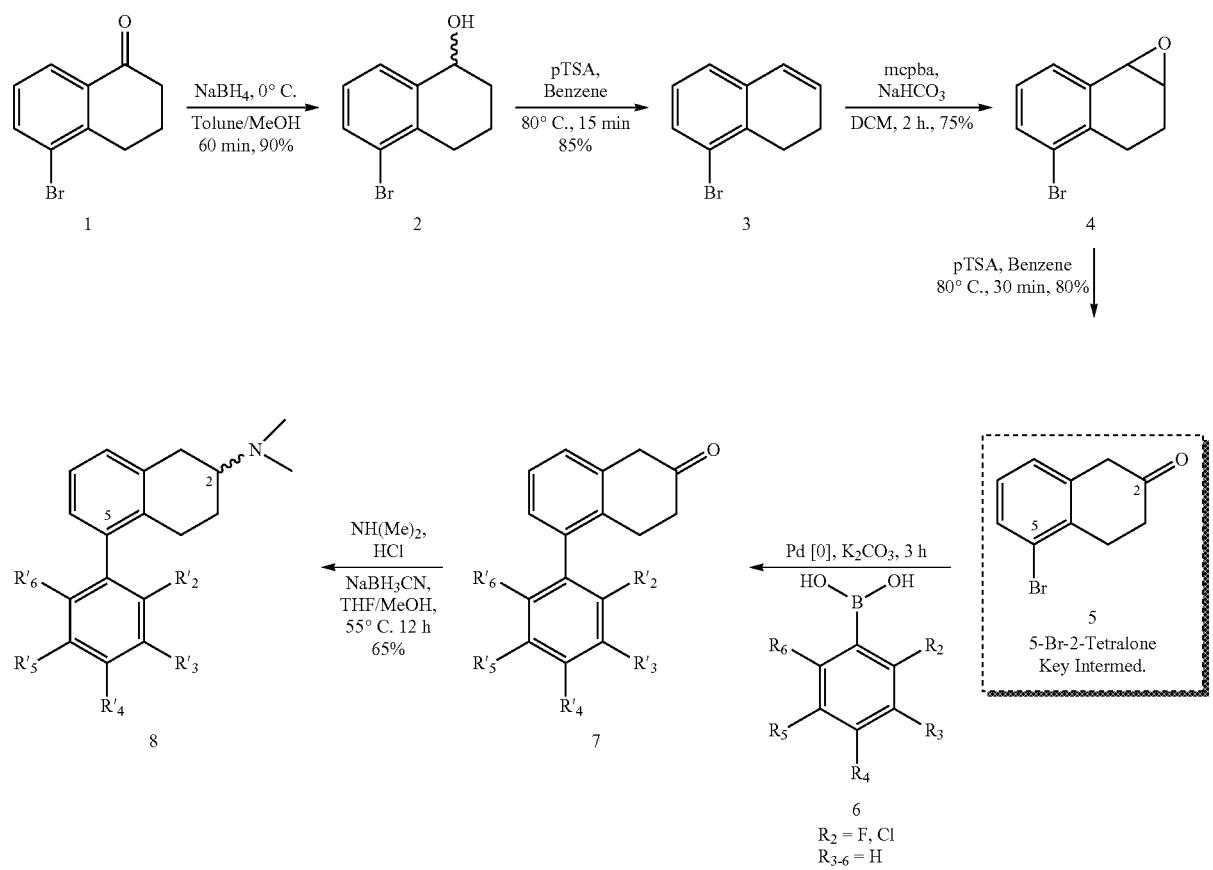

was reduced to give the corresponding alcohol (2) that was treated with pTSA to obtain the olefin (3) to obtain the epoxide (4), that was treated with pTSA to obtain key intermediate 5-Br-2-tetralone (5). 5-Br-2-tetralone can be reacted with a wide variety of commercially-available boronic acid derivatives (6), these organoboron when used in the Suzuki-Miyaura cross coupling reaction allow synthesis of the compounds described herein. Thus, in Scheme 1, 5-bromo-2-tetralone (5) was reacted with Tetrakis triph- In addition, the boronic acid derivatives in Chart 1 are available to synthesize the corresponding 5-substituted-PAT analogs, according to Scheme 1. Thus analogs are proposed with multiple substitutions to the 5-phenyl moiety, as listed under Hydrogen and Halogen Binding Moieties in Chart 1. Thus, racemic analogs will be synthesized and separated to yield (+)- and (−)-5 (2R)-5-PAT analogs and/or (2R) and (2S)-5-PAT analogs.

CHART 1

| Hydrogen and Halogen Binding Moieties | Hydrophobic and Aromatic |
| --- | --- |
| 2-aminophenylboronic acid | cyclopropylboronic acid |
| 3-aminophenylboronic acid | cyclopentylboronic acid |
| 4-aminophenylboronic acid | 4-tert-butylcyclohex-1-en-1-ylboronic acid |
| 4-acetamidophenylboronic acid | cyclohept-1-en-1-ylboronic acid |
| 2-acetylphenylboronic acid | biphenyl-2-sulfonic acid |
| 3-acetylphenylboronic acid | biphenyl-3-ylboronic acid |
| 4-acetylphenylboronic acid | biphenyl-4-ylboronic acid |
| 4-isocyanatophenylboronic acid | anthracen-9-ylboronic acid |
| 2-(methoxycarbonylamino)phenylboronic acid | 2,3-dihydrobenzo[b][1,4]dioxin-6-ylboronic acid |
| 3-(acetamidomethyl)phenylboronic acid | 1,4-dioxaspiro[4.5]dec-7-en-8-ylboronic acid |
| 3-amino-4-boronobenzoic acid | |

CHART 1-continued

| Hydrogen and Halogen Binding Moieties | Hydrophobic and Aromatic |
|---|---|
| 3-amino-5-carboxyphenylboronic acid | |
| 4-acetoxyphenylboronic acid | |
| 4-(ethoxycarbonylmethyl)phenylboronic acid | |
| 3-acetamido-5-carboxyphenylboronic acid | |
| 2-carbamoylphenylboronic acid | |
| 2,6-bis(trifluoromethyl)phenylboronic acid | |
| 3,5-bis(trifluoromethyl)phenylboronic acid | |
| 2,4-bis(trifluoromethyl)phenylboronic acid | |
| 2-(aminomethyl)-4-fluorophenylboronic acid | |
| 2-(aminomethyl)-5-fluorophenylboronic acid | |
| 3-amino-4-chlorophenylboronic acid | |

CHART 1-continued

| Hydrogen and Halogen Binding Moieties | Hydrophobic and Aromatic |
|---|---|

[Structures of boronic acid compounds shown in the chart:
- 3-carbamoylphenylboronic acid (H2N-C(=O)-C6H4-B(OH)2)
- 2-nitro-3-acetamidophenylboronic acid
- 4-cyano-2-aminophenylboronic acid hydrochloride
- 3-cyano-5-aminophenylboronic acid hydrochloride
- 3-(tert-butylaminosulfonyl)phenylboronic acid (CH3(CH3)3NHSO2-C6H4-B(OH)2)
- 3-(tert-butylaminosulfonyloxy)phenylboronic acid ((CH3)3CNHSO3-C6H4-B(OH)2)
- 4-(tert-butylaminosulfonylmethyl)phenylboronic acid (CH2(CH3)3NHSO2-C6H4-B(OH)2)
- 3-carbamoyloxyphenylboronic acid (H2NCO-C6H4-B(OH)2)]

Example 2: 4-PAT Synthesis

Synthesis of compounds of Formula II is described in WO 2010/1290048, for example "Synthetic Schemes" of pages 53-55, and WO 2008/156707, for example 11 of pages 53-57, the entire contents of which are hereby incorporated by reference.

Example 3: Derivitization of the Amino Group at the 2 Position of the Tetralin Core Any of the compounds described herein may be derivatized at an amino group at 2 position of the tetralin core via the reaction shown below:

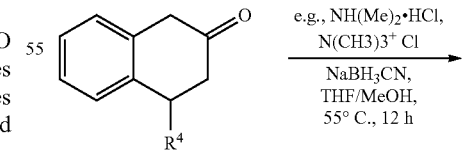

e.g., $NH(Me)_2 \cdot HCl$, $N(CH_3)_3^+ Cl^-$ $NaBH_3CN$, THF/MeOH, 55° C., 12 h

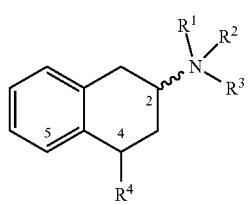

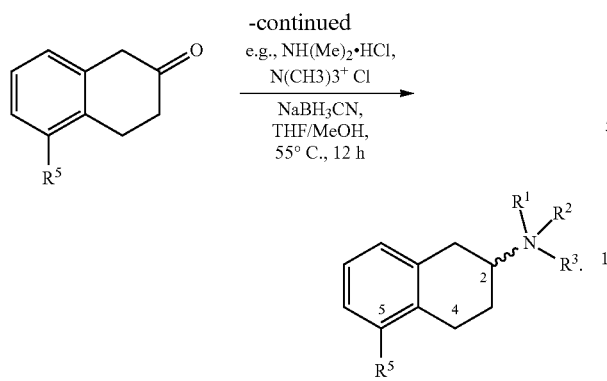

Example 4: (+)-5-FPT is Orally Active And Readily Crosses the Blood-Brain Barrier The compound (+)-5-FPT (5-(2'-fluorophenyl)-N,N-dimethyl-1,2,3,4-tetrahydronaphthalen-2-amine) falls outside of Formula I as is lacks a positive charge on the nitrogen bearing $R^1$, $R^2$, and $R^3$:

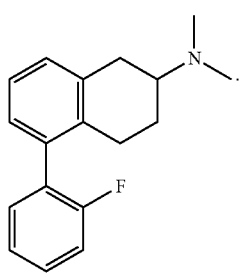 [SMILES: CN(C)C1CCc2c(cccc2-c2ccccc2F)C1]

Adult, male, C57Bl/6J mice, approximately six months old, and treatment-naïve for at least six weeks prior to testing, were injected subcutaneously with (+)-5-FPT (3.0 mg/kg) and returned to their home cages. At 30, 60, or 90 min later, mice were euthanized by rapid cervical dislocation and decapitation. Trunk blood was collected in pre-chilled, heparin-coated tubes. Brains were quickly excised and frozen in liquid nitrogen. Plasma was collected from blood after centrifugation for 5 min at 13,000 g. Whole brain samples were wrapped in foil, and brain and plasma samples were labeled and stored at −80° C. until liquid chromatography-mass spectrometry/mass spectrometry (LC-MS/MS) assays were performed. Frozen brain samples were weighed and homogenized in phosphate buffered saline (PBS), pH 7.4. After the first analysis, the extra brain homogenate was stored at −80° C. until they were thawed for a second, more dilute, analysis. Plasma samples were used directly upon arrival. The proteins from each plasma sample and a portion of each brain homogenate were immediately precipitated with 1:1 methanol:acetonitrile (4× starting volume) and internal standard ((−)-MBP[68]) followed by centrifugation at 14,000 g for 5 minutes at 4° C. The resulting supernatants from each sample were dried under nitrogen. Each sample was reconstituted in methanol, vortexed, sonicated briefly, and centrifuged prior to LC-MS/MS analysis. Calibration curves were constructed from the ratios of the peak areas of 5-FPT versus (−)-MBP in extracted standards made in mouse plasma or homogenized mouse brain.

LC-MS/MS analysis was performed using an Agilent 1100 series HPLC and a Thermo Finnigan Quantum Ultra triple quad mass spectrometer. The mobile phases used were 0.1% formic acid in water (A) and 0.1% formic acid in methanol (B) in a 5 minute gradient. Samples of 10 μL each were injected onto a Phenomenex Gemini C18 column (2×50 mm, 5μ) with a C18 guard column. 5-FPT and its internal standard ((−)-MBP) were ionized in ESI+ and detected in SRM mode. Internal standards were used for quantification of the compound level per g tissue or per μL plasma. Four mice were included per group, but plasma levels from one mouse were not detectable due to low volume of blood collected.

Unlike compounds of the present invention, (+)-5-FPT readily crosses the blood-brain barrier, as evidenced by detection of μg levels 30, 60, and 90 min after systemic administration (Table 4). Notably, levels of (+)-5-FPT were substantially lower in plasma relative to brain tissue as soon as 30 min post-administration, indicating that (+)-5-FPT is rapidly cleared in the periphery. Meanwhile, the attenuating effects of (+)-5-FPT (5.6 mg/kg) on the DOI HTR remained significant for up to 2 hrs. post-administration; at 3 hrs. post-administration, (+)-5-FPT did not block the DOI HTR.

TABLE 4

Plasma and brain concentrations of (+)-5-FPT after 3.0 mg/kg subcutaneous administration. Data are expressed as mean (SEM).

| | Time after injection | | |
|---|---|---|---|
| | 30 min | 60 min | 90 min |
| Plasma (μg/mL) | 0.114(0.03) | 0.118(0.01) | 0.070(0.01) |
| Brain (μg/g) | 1.78(0.24) | 2.16(0.17) | 1.46(0.09) |

Example 5: Compounds Bearing a Positively Charged Amino Group at the 2 Position of the Tetralin Core do not Readily Cross the Blood-Brain Barrier Adult, male, C57Bl/6J mice, approximately six months old, and treatment-naïve for at least six weeks prior to testing, are injected sc with any of the compounds described above, bearing a positively charged amino group at the 2 position of the tetralin core (the "test compound") at a dose of about 3.0 mg/kg and returned to their home cages. At 30, 60, or 90 min later, mice are euthanized by rapid cervical dislocation and decapitation. Trunk blood is collected in pre-chilled, heparin-coated tubes. Brains are quickly excised and frozen in liquid nitrogen. Plasma is collected from blood after centrifugation for 5 min at 13,000 g. Whole brain samples are wrapped in foil, and brain and plasma samples are labeled and stored at −80'C until liquid chromatography-mass spectrometry/mass spectrometry (LC-MS/MS) assays are performed.

Frozen brain samples are weighed and homogenized in phosphate buffered saline (PBS), pH 7.4. After the first analysis, the extra brain homogenate is stored at −80'C until they are thawed for a second, more dilute, analysis. Plasma samples are used directly upon arrival. The proteins from each plasma sample and a portion of each brain homogenate are immediately precipitated with 1:1 methanol:acetonitrile (4× starting volume) and internal standard (e.g. (−)-MBP[68]) followed by centrifugation at 14,000 g for 5 minutes at 4° C. The resulting supernatants from each sample are dried under nitrogen. Each sample is reconstituted in methanol, vortexed, sonicated briefly, and centrifuged prior to LC-MS/MS analysis. Calibration curves are constructed from the ratios of the peak areas of test compound versus internal standard in extracted standards made in mouse plasma or homogenized mouse brain.

LC-MS/MS analysis is performed using an Agilent 1100 series HPLC and a Thermo Finnigan Quantum Ultra triple quad mass spectrometer. The mobile phases used are 0.1% formic acid in water (A) and 0.1% formic acid in methanol (B) in a 5 minute gradient. Samples of 10 µL each are injected onto a Phenomenex Gemini C18 column (2×50 mm, 5µ) with a C18 guard column. The test compound and its internal standard ((−)-MBP) were ionized in ESI+ and detected in SRM mode. Internal standards are used for quantification of the test compound level per g tissue or per µL plasma.

The test compounds are not expected to accumulate in the brain and, rather, are expected to be more prevalent in the plasma.

Example 6: 5-HT$_7$ Receptor Binding Affinity of 5-PAT Compounds

Table 5 shows a group of 5-PAT compounds that were synthesized and tested for their in vitro binding affinity to serotonin 5-HT$_7$ receptors using human embryonic kidney 293 (HEK293) cells as described in Canal et al., ACS Chem. Neurosci. 2015, 6, 1259-1270. The compounds are tertiary amines and available to bind 5-HT$_7$ receptors both in the brain and in the periphery. Each of the compounds can be derivatized to a corresponding positively-charged quaternary amine, for example, by the addition of a third alkyl group, R$_3$, to render it impermeable to the blood-brain barrier and specific for peripheral 5-HT$_7$ receptors.

TABLE 5

5-Substituted-2-aminotetralins.

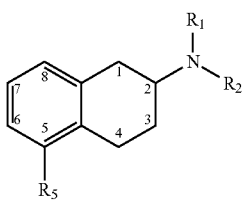

| R$_1$/R$_2$ Substituent | R$_5$ Substituent | Human 5-HT$_7$Ki (nM) |
|---|---|---|
| (S)-Methyl | Phenyl | 9 ± 0.4 |
| (R)-Methyl | Phenyl | 4400 ± 930 |
| (S)-Methyl | Phenyl-2'-F | 6 ± 0.7 |
| (R)-Methyl | Phenyl-2'-F | 260 ± 53 |
| (S)-Methyl | Phenyl-2'-Cl | 6 ± 0.6 |
| (R)-Methyl | Phenyl-2'-Cl | 58 ± 12 |
| (R/S)-Methyl | Phenyl-2'-NH$_3$ | 91 ± 6.8 |
| (R/S)-Methyl | Phenyl-3'-F | 34 ± 6.2 |
| (R/S)-Methyl | Phenyl-3'-Cl | 18 ± 2.4 |
| (R/S)-Methyl | Phenyl-3'-CF$_3$ | 63 ± 6.6 |
| (R/S)-Methyl | Phenyl-3'-OMe | 37 ± 9.0 |
| (R/S)-Methyl | Phenyl-3',5'-F | 180 ± 32 |
| (R/S)-Methyl | Phenyl-3',5'-Cl | 40 ± 60 |
| (S)-Methyl | Phenyl-3',5'-CF$_3$ | 910 ± 260 |
| (R)-Methyl | Phenyl-3',5'-CF$_3$ | >10,000 |
| (R/S)-Methyl | Phenyl-4'-F | 120 ± 17 |
| (S)-Methyl | Pheny-4'-Cl | 72 ± 5.8 |
| (R/S)-Methyl | Phenyl-2'-Cl-4'-F | 30 ± 10 |
| (S)-Methyl | Napthalene | 17 ± 2.4 |
| (R)-Methyl | Napthalene | 28 ± 5.1 |
| (S)-Methyl | Furanyl | 33 ± 2.5 |

TABLE 5-continued

5-Substituted-2-aminotetralins.

| R$_1$/R$_2$ Substituent | R$_5$ Substituent | Human 5-HT$_7$Ki (nM) |
|---|---|---|
| (R)-Methyl | Furanyl | >10,000 |
| (R/S)-Methyl | Cyclopentyl | 240 ± 35 |
| (R/S)-Methyl | Anthracene | 440 ± 110 |
| (R/S)-Methyl | Isoquinoline | 93 ± 10 |
| (R/S)-Methyl | O-Benzyl | >10,000 |
| (S)-Propyl | 2'-F-Phenyl | 35 ± 5.2 |
| (R)-Propyl | 2'-F-Phenyl | 63 ± 2.7 |
| (R)-Propyl | Phenyl | 180 ± 31 |
| (S)-Propyl | Phenyl | 83 ± 5.8 |
| (R/S)-Methyl | 7,8-diOMe-5-Phenyl | >10,000 |

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A compound that is a 5-HT receptor modulator having the structure of Formula (I):

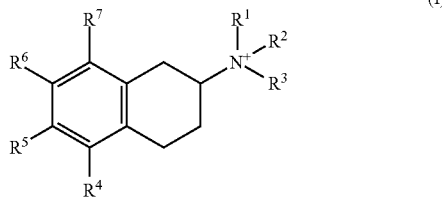

or pharmaceutically acceptable salt thereof, wherein:
  each of $R^1$, $R^2$, and $R^3$ is independently a substituent,
  each of $R^5$, $R^6$, and $R^7$ is independently hydrogen or a substituent, and
  $R^4$ is an optionally substituted carbocyclic or heterocyclic ring system.

2. The compound of claim 1, wherein the compound does not substantially accumulate in the human brain.

3. The compound of claim 1, wherein the compound is a modulator of one or more of 5-HT$_1$ receptors (e.g. one or more of 5-HT$_{1A}$, 5-HT$_{1B}$, 5-HT$_{1C}$, 5-HT$_{1D}$, 5-HT$_{1E}$, 5-HT$_{1F}$), 5-HT$_2$ receptors (e.g. one or more of 5-HT$_{2A}$, 5-HT$_{2B}$, 5-HT$_{2C}$); 5-HT$_3$ receptors; 5-HT$_4$ receptors; 5-HT$_5$ receptors (e.g. 5-HT$_{5A}$); 5-HT$_6$ receptors; and HT$_7$ receptors.

4. The compound of claim 1, wherein the modulation is selected from full agonism, partial agonism, antagonism, inverse agonism and inhibition.

5. The compound of claim 1, wherein the compound is a dual partial agonist at the serotonin 5-HT$_7$ and 5-HT$_{1A}$ receptors.

6. The compound of claim 1, wherein the compound is a modulator of one or more of the serotonin 5-HT$_{2A}$, 5-HT$_{2B}$, and 5-HT$_{2C}$ receptors.

7. The compound of claim 6, wherein the compound selectively inhibits the serotonin 5-HT$_{2C}$ receptor relative to 5-HT$_{2A}$ or 5-HT$_{2B}$.

8. The compound of claim 1, wherein the compound is enantiomerically pure.

9. The compound of claim 1, wherein each of $R^1$, $R^2$, and $R^3$ are methyl.

10. The compound of claim 1, wherein $R^5$, $R^6$, and $R^7$ are each independently hydrogen, alkyl, aryl, halo, nitro, amino, heteroaryl, cycloalkyl, heterocyclic, or alkoxy.

11. The compound of claim 1, wherein $R_4$ is an optionally substituted phenyl, naphthyl, or furan ring.

12. The compound of claim 11, wherein $R_4$ is substituted with one or more alkyl, alkoxy, or halo substituents.

13. The compound of claim 11, wherein $R_4$ is phenyl substituted with one fluoro or chloro.

14. The compound of claim 13, wherein $R_4$ is ortho-fluoro or ortho-chloro substituted phenyl.

15. The compound of claim 11, wherein $R_4$ has a methyl or methoxy substituent.

16. The compound of claim 15, wherein $R_4$ is meta-methyl or meta-methoxy substituted phenyl.

17. The compound of claim 11, wherein $R_4$ is unsubstituted naphthyl.

18. The compound of claim 1, wherein the compound is not a physiologically-relevant substrate for one or more forms of P450, selected from CYP1A2, CYP2C19, CYP2C9, CYP2D6, CYP2E1, and CYP3A4.

19. A pharmaceutical composition comprising a therapeutic amount of the compound of claim 1, and a pharmaceutically acceptable excipient or carrier.

20. The pharmaceutical composition of claim 19, wherein the compound is substantially enantiomerically pure.

21. A method for treating a gastrointestinal disorder or condition, comprising administering the compound of claim 1 to a patient in need thereof.

22. The method of claim 21, wherein the gastrointestinal disorder or condition is selected from inflammatory bowel disease, irritable bowel syndrome, celiac disease, and an enteric infection.

23. The method of claim 21, wherein the patient has Crohn's Disease or ulcerative colitis.

24. A method for treating a cardiopulmonary disorder, comprising administering the composition of claim 1 to a patient in need thereof.

25. The method of claim 24, wherein the cardiopulmonary disorder is one or more of cardiac valvulopathy and pulmonary hypertension.

26. The compound of claim 14, wherein the compound is (2S)-5-(2'-fluorophenyl)-N,N,N-trimethyl-tetrahydronaphthalen-2-amine.

27. The pharmaceutical composition of claim 19, wherein the compound is (2S)-5-(2'-fluorophenyl)-N,N,N-trimethyl-tetrahydronaphthalen-2-amine.

28. The method of claim 21, wherein the compound is (2S)-5-(2'-fluorophenyl)-N,N,N-trimethyl-tetrahydronaphthalen-2-amine.

* * * * *

UNITED STATES PATENT AND TRADEMARK OFFICE
CERTIFICATE OF CORRECTION

PATENT NO. : 10,548,856 B2
APPLICATION NO. : 15/574971
DATED : February 4, 2020
INVENTOR(S) : Raymond G. Booth Page 1 of 1

It is certified that error appears in the above-identified patent and that said Letters Patent is hereby corrected as shown below:

In the Specification

Column 1, Line 10, please insert the following:
--STATEMENT REGARDING FEDERALLY SPONSORED RESEARCH OR DEVELOPMENT
This invention was made with government support under grant numbers DA030989 and MH081193 awarded by the National Institutes of Health. The government has certain rights in the invention.--

Signed and Sealed this
Seventeenth Day of March, 2020

Andrei Iancu
*Director of the United States Patent and Trademark Office*